United States Patent [19]

Parenteau et al.

[11] Patent Number: 5,374,515
[45] Date of Patent: Dec. 20, 1994

[54] IN VITRO CORNEA EQUIVALENT MODEL

[75] Inventors: Nancy L. Parenteau, Brookline; Valerie S. Mason, Littleton; Bjorn R. Olsen, Milton, all of Mass.

[73] Assignees: Organogenesis, Inc., Canton; The President and Fellows of Harvard College, Cambridge, both of Mass.

[21] Appl. No.: 974,740

[22] Filed: Nov. 13, 1992

[51] Int. Cl.$^5$ .......................... A01N 1/02; C12N 5/00; A61F 2/14

[52] U.S. Cl. .................... 435/1; 435/240.23; 435/240.241; 623/5

[58] Field of Search ............... 435/1, 240.23, 240.241; 623/5

[56] References Cited

U.S. PATENT DOCUMENTS

| | | | |
|---|---|---|---|
| 4,485,096 | 11/1984 | Bell | 514/21 |
| 4,546,500 | 10/1985 | Bell | 435/1 |
| 4,760,020 | 7/1988 | Neufeld et al. | 435/29 |
| 5,131,907 | 7/1992 | Williams et al. | 435/240.2 |

OTHER PUBLICATIONS

Xie, et al., "A simplified . . . cells," In Virto Cellular & Developmental Biology, 25:20–22 (1989).
Simmons, et al., "Corneal . . . irritancy," Toxicology and Applied Pharmacology, 88:13–23 (1987).
Zieske, J. D., Bukysoglu, G., Yankauckas, M. A., "Characterization of a . . . cells," Invest. Opthalmol. Vis. Sci., 33:143–152 (1992).
Schermer, A., Galvin S., and Sun, T. T., "Differentiation-related . . . cells," J. Cell Bio., 103:49 (1986).
Muragaki, Y., et al., "Alpha-1-VIII collagen . . . tissues," Eur J. Biochem., 207(3):895–902 (1992).
Insler, M. S. and Lopez, J. G., "Transplantation of . . . endothelium," Curr. Eye Res., 5(12):967–72 (1986).
Roat, M. I. and Thoft, R. A., "Ocular surface . . . transplantation" Int. Opthalmol. Clin., 28(2):169–174 (1988).
Parish, W. E., "Ability of . . . inflammation," Fd. Chem. Toxic. 23.215–27 (1985).
Gordon, V. C. and Kelly, C. P., "An in vitro method . . . irritation," Cosmetics & toiletries, 104:69–74 (1989).
Goldberg, A. M., "An approach to . . . methods," Fd. Chem. Toxic., 23:205–208 (1985).
Shopsis, C., et al., "A battery of . . . cytology," Fd. Chem. Toxic., 23:259–66 (1985).
Eliason, J. A. and J. P. Elliott, "Proliferation of . . . epithelium," Investigative Ophthalmol. & Visual Science, 28:1963–69 (1987).
Trinkaus-Randall, V., et al., "Influence of substratum . . . synthesis," Investig. Ophthal. & Visual Science, 29:1800–1809 (1988).
Sundar-Raj, C. V., et al., "selective growth . . . synthesis," Invest. Ophthalmol. 19:1222–30 (1980).
Insler, et al.; Current Eye Research, vol. 5, No. 12, pp. 967–972; 1986.

Primary Examiner—Douglas W. Robinson
Assistant Examiner—Susan M. Dadio
Attorney, Agent, or Firm—Hollie L. Baker

[57] ABSTRACT

This invention is directed to an organ equivalent of the cornea part of the eye made using tissue culturing systems. The method of constructing the cornea equivalent results in a structure analogous to the eye cornea in vivo. The cornea equivalent is an in vitro model of the eye, which can be used for transplantation or implantation in vivo or for screening compounds in vitro.

28 Claims, 13 Drawing Sheets

FIG. 6A
FIG. 6B
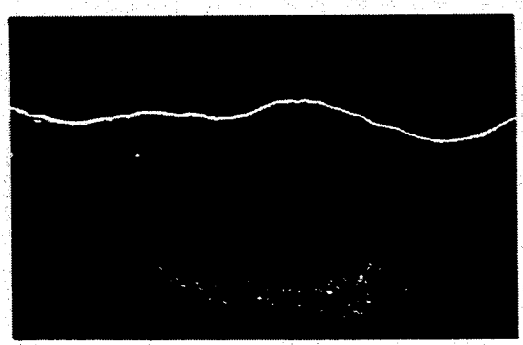
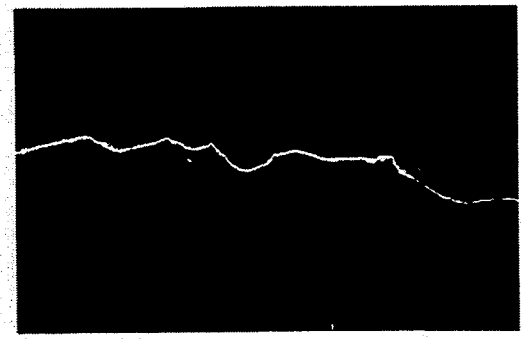
FIG. 6C
FIG. 6D
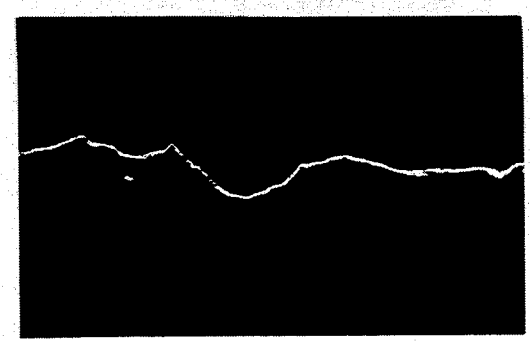
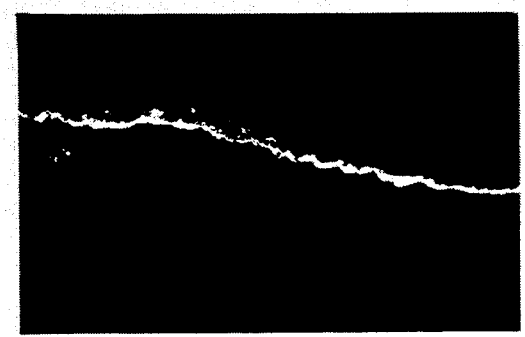
FIG. 6E
FIG. 6F

IN VITRO CORNEA EQUIVALENT MODEL

FIELD OF THE INVENTION

This invention is in the field of tissue culture systems and is directed to an organ equivalent of the cornea of the eye: a cornea equivalent model. The tissue culture method of constructing the cornea equivalent model results in a construct analogous to the eye cornea in vivo. The cornea equivalent is an in vitro model of the eye, which can be used for transplantation or implantation in vivo or for screening compounds in vitro.

BACKGROUND OF THE INVENTION

Tissue culture techniques are being successfully used in developing tissue and organ equivalents. The basis for these techniques involve collagen matrix structures, which are capable of being remodeled into functional tissue and organs by the right combination of living cells, nutrients, and culturing conditions. Tissue equivalents have been described extensively in many patents, including U.S. Pat. Nos. 4,485,096; 4,485,097; 4,539,716; 4,546,500; 4,604,346; and 4,837,379, all of which are incorporated herein by reference. One successful application of the tissue equivalent is the living skin equivalent, which has a morphology similar to actual human skin. The living skin equivalent is composed of two layers: the upper portion is made of differentiated and stratified human epidermal keratinocytes that cover a thicker, lower layer of human dermal fibroblasts in a collagen matrix. Bell, et al., "Recipes for Reconstituting Skin," *J. of Biochemical Engineering*, 113: 113–119 (1991).

Studies have been done on culturing corneal epithelial and endothelial cells. Xie, et al., "A simplified technique for the short-term tissue culture of rabbit corneal cells," *In Vitro Cellular & Developmental Biology*, 25: 20–22 (1989), and Simmons, et al., "Corneal Epithelial Wound Closure in Tissue Culture: An in vitro Model of Ocular Irritancy," *Toxicology and Applied Pharmacology*, 88: 13–23 (1987). Developing an in vitro organ equivalent of the cornea of the eye is of particular interest for use in in vitro toxicity assays to serve as accurate and inexpensive non-animal predictive models of in vivo ocular and dermal irritation potential for many types of products and raw materials.

SUMMARY OF THE INVENTION

This invention is directed to an organ equivalent of the cornea of the eye. Constructing the cornea equivalent according to this invention involves the generation by tissue culture of the three distinct cell layers in the cornea: the external layer, a stratified squamous epithelium; the middle layer, collagen fibers; and the inner layer, a simple squamous epithelium, also called the corneal endothelium. The method of constructing the cornea equivalent results in a structure analogous to the eye cornea in vivo.

This invention is based, in part, on the discovery that the inclusion of an endothelial layer is required, not only for corneal transparency in vivo, but also for improved morphology, expression of biochemical and physiological markers, cell spreading, epithelial attachment to the matrix, and uniformity of epithelial coverage in vivo. The endothelium promotes basement membrane development in the cornea equivalent. The results on the influence of the endothelium in achieving a higher level of epithelial differentiation in vitro was unexpected.

Based on this discovery, it was found that the use of the endothelium in other tissue and organ equivalents also promotes basement membrane development. Thus, this invention is also directed to the use of an endothelial cells in those tissue and organ equivalent constructs that use collagen or epithelial cells.

DESCRIPTION OF THE FIGURES

FIG. 2A: Submerged, 200X
FIG. 2B: Air-lift moist interface, 400X
FIG. 2C: Air-lift dry, 200X.

FIG. 3A: Submerged, 200X
FIG. 3B: Air-lift moist, 200X
FIG. 3C: Air-lift moist, 400X
FIG. 3D: Air-lift dry, 200X.

FIG. 4A: Submerged, 200X
FIG. 4B: Air-lift moist, 200X
FIG. 4C: Air-lift dry, 200X
FIG. 4D: Air-lift dry, phase of left, 200X.

FIGS. 6A, 6B, 6C, 6D, 6E and 6F show immunofluorescence photomicrographs of corneal equivalents showing the distribution of Laminin and Type VII in corneal equivalents with and without an endothelial cell layer. Corneal constructs after 14 days at a moist interface without an endothelial layer, exhibit a small amount of laminin (6A) and type VII collagen (6B). When the endothelial layer is incorporated (6C, 6D, 6E, 6F) in the construct, laminin (6C) and type VII collagen (6D, 6E, 6F) are present in an unbroken line at the stromal-epithelial junction.

FIG. 6A: Air-lift moist, laminin, 400X
FIG. 6B: Air-lift moist, type VII, 400X
FIG. 6C: Air-lift moist plus endo, laminin, 100X
FIG. 6D: Air-lift moist plus endo, type VII, 100X
FIG. 6E: Air-lift moist plus endo, type VII, 200X
FIG. 6F: Air-lift moist plus endo, type VII, 400X.

FIG. 7 is a transmission electron micrograph showing no evidence of abnormal squamous differentiation after culture at the moist interface. The construct epithelium had a columnar basal layer and stratified suprabasal cells with no morphologic evidence of differentiation. Bar=2 um.

FIG. 8 is a transmission electron micrograph showing formation of basal lamina in tri-layered corneal equivalents. A basal lamina was observed at the stromal-epithelial junction with numerous hemidesmosomes (asterisks), a well-defined lamina densa (large arrowheads), anchoring filaments (small arrowheads) and associated anchoring plaques (arrows). The stroma directly beneath the basal lamina (SM) consisted of a mix of collagen fibrils (white arrow) and short fine fibrils (white arrowheads) which are characteristic of Bowman's Membrane. Bar=0.1um.

FIG. 9 is a transmission electron micrograph showing vermiform ridges on the epithelial surface. The apical cells of the culture expressed vermiform ridges along the anterior surface (arrowheads). Bar=1 um.

FIG. 10 is a transmission electron micrograph of lanthanum-treated tri-layered corneal equivalents showing the presence of tight junctions. Tight junctions were observed between cells was in the apical layers of the epithelium (arrowheads). Bar=0.1 um.

DETAILED DESCRIPTION OF TEE INVENTION

Figure 1A:
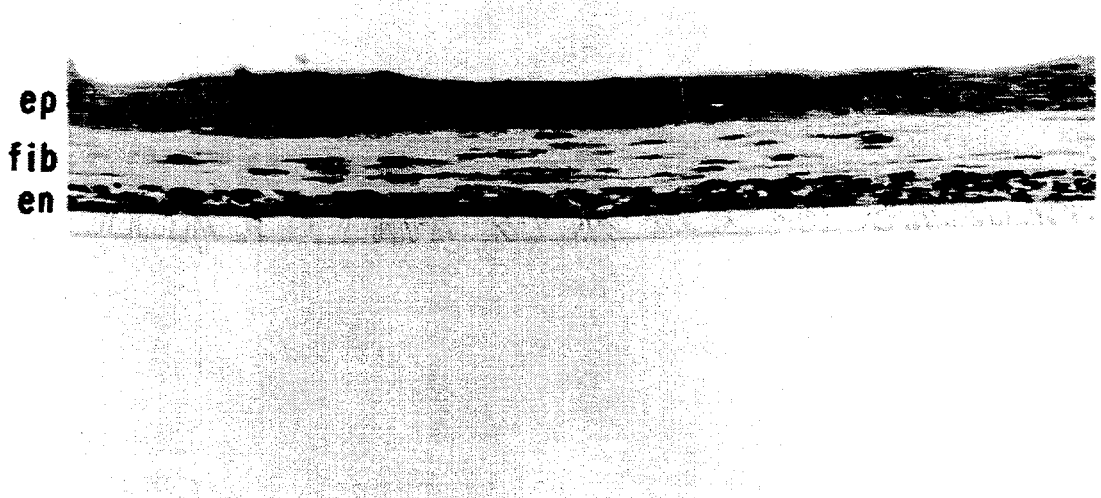
FIGS. 1A and 1B show photomicrographs A and B of cornea equivalents formed with and without an endothelial cell layer. Photomicrograph A of the three-cell corneal construct was taken after 14 days at a moist interface. The normal rabbit epithelium (EP) consists of approximately seven layers of cells. Due to the presence of the multilayered transformed mouse endothelial layer (EN), the normal rabbit stromal fibroblasts (FIB) are not hyperproliferative. This allows for epithelial attachment and eliminates the development of a fibroblast skin. Without an endothelial layer (B) the epithelium is poorly attached and varies in thickness and organization. Mag=160X
Figure 1B:
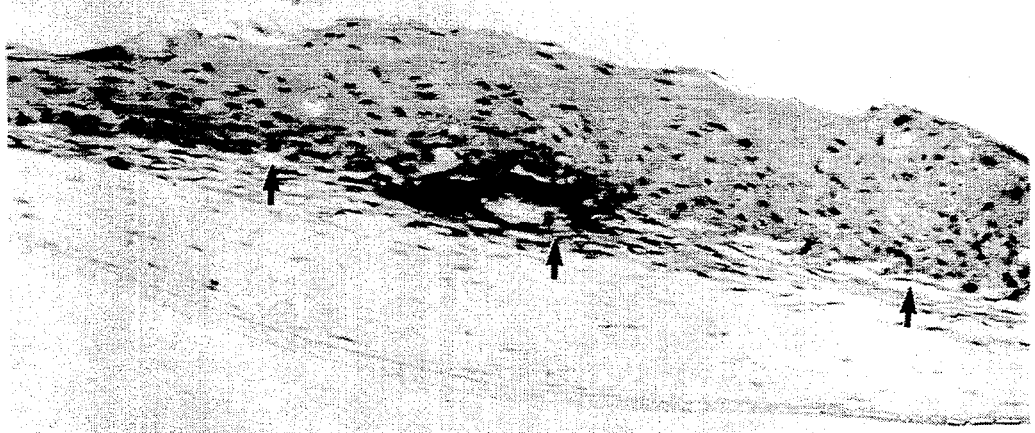
Figure 2A:
FIGS. 2A, 2B and 2C show photomicrographs of corneal equivalents after being cultured submerged, at a moist interface and at a dry interface. The photomicrographs show the histological appearance of corneal equivalents cultured under different environmental conditions. Plastic sections stained with hematoxylin and eosin show the different morphologies obtained using different culture environments. When the epithelial cells are grown on the lattice for 14 days in a submerged culture (2A), the result is a minimally organized thickened epithelium. This epithelium will also vary in thickness due to the uneven spreading of the epithelial cells. If the culture is raised to a moist interface, the epithelium becomes more organized (2B). When raised to a dry interface, stratum corneum-like layers develop (2C), as evidenced by many layers of cornified cells.
Figure 2C:
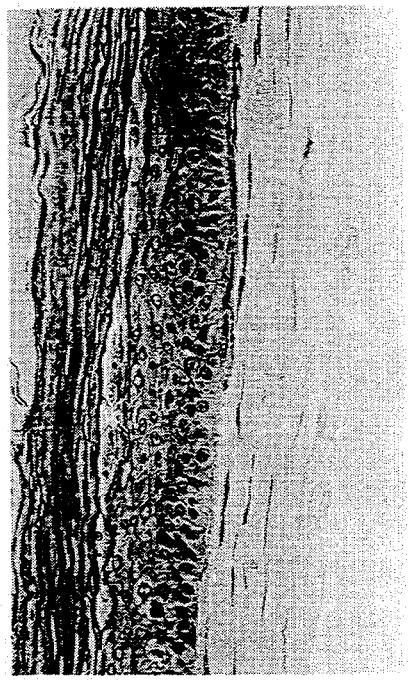
Figure 2B:
Figure 3B:
FIGS. 3A, 3B, 3C and 3D show immunofluorescent photomicrographs of the distribution of enolase under different environmental conditions. The photomicrographs depict 14 day corneal constructs showing a change in enolase staining. Enolase is a marker for the proliferative cell population in corneal epithelium. It is normally present in basal cells of the limbal region (Zieske, 1992). The entire epithelium stains positively for enolase when the culture is submerged (3A) indicating a hyperproliferative state and lack of specialization or differentiation. When the culture is raised to either a moist (3B, 3C) or dry interface (3D), staining is reduced in the suprabasal layers too more closely approximate what is observed in vivo.
Figure 3D:
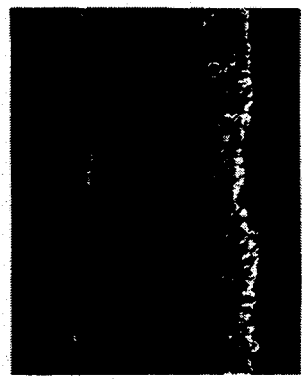
Figure 3A:
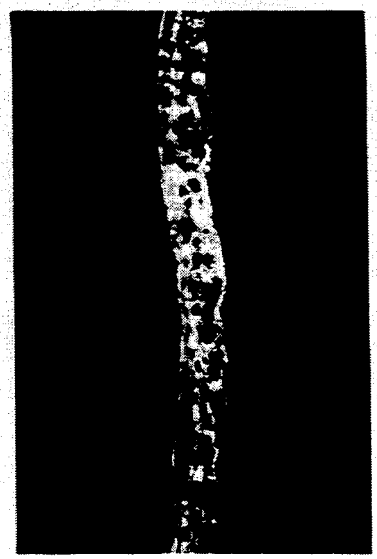
Figure 3C:
Figure 4A:
FIGS. 4A, 4B, 4C and 4D are immunofluorescent photomicrographs showing the distribution of keratin 3 under different environmental conditions. Keratin 3 is a marker specific for corneal epithelial cells and is normally present in all suprabasal cell layers of the corneal limbus and the cells of the central cornea (Shermer et al., 1986). The 14 day corneal equivalents cultured submerged exhibit small amounts of keratin 3 labeling (labeled using AE5 antibody in a few of the most superficial cells (4A). When cultures are raised to either a moist or dry interface (4B, 4C, 4D), staining is strong and now present in all suprabasal layers as in normal corneal limbus in vivo.
Figure 4B:
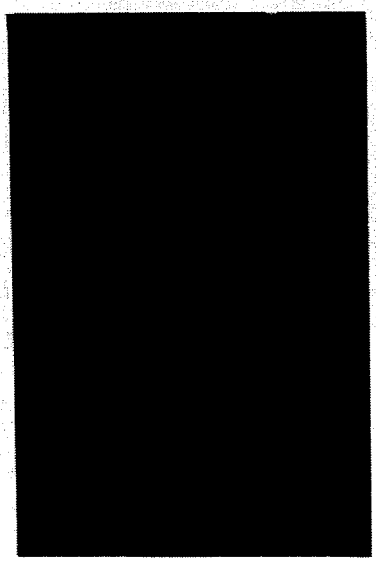
Figure 4C:
Figure 4D:
Figure 5A:
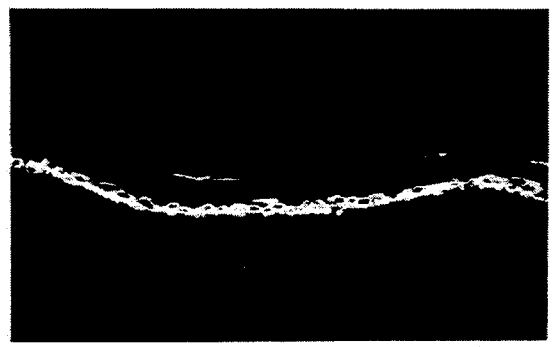
FIGS. 5A, 5B, 5C and 5D are immunofluorescence photomicrographs showing the difference in enolase, keratin 3 and vinculin distribution with and without an endothelial cell layer. Corneal equivalents containing the endothelial layer after being at a moist interface for 14 days exhibit proper distribution of alphaenolase (5A) (Zieske et al., 1992) and keratin 3 (labeled by antibody AE5, (Shermer et al., 1986) (5D) staining. The overproduction of vinculin in a sample that has been at the moist interface without an endothelial layer (5B) is reduced to punctate staining in a sample that has an endothelial layer (5C). Mag=200X FIG. 5A: Moist airlift plus endothelial layer; Alpha enolase
FIG. 5B: Moist airlift: Vinculin
FIG. 5C: Moist airlift plus endothelial layer; Vinculin
FIG. 5D: Moist airlift plus endothelial layer; AE5.
Figure 5B:
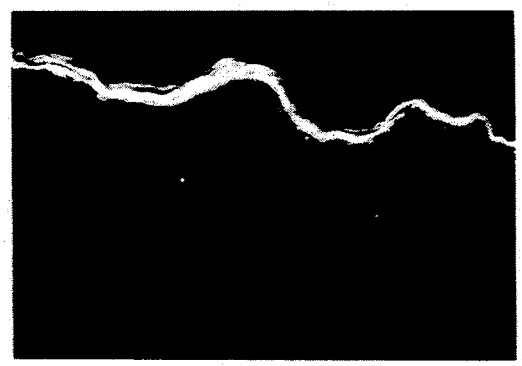
Figure 5C:
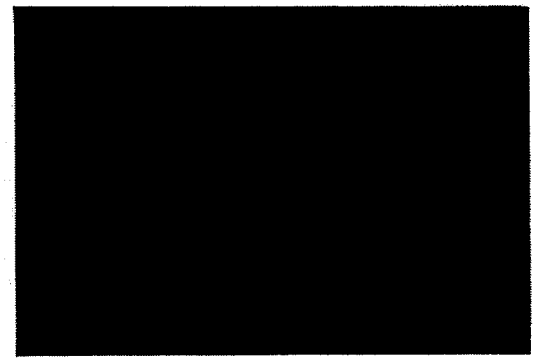
Figure 5D:
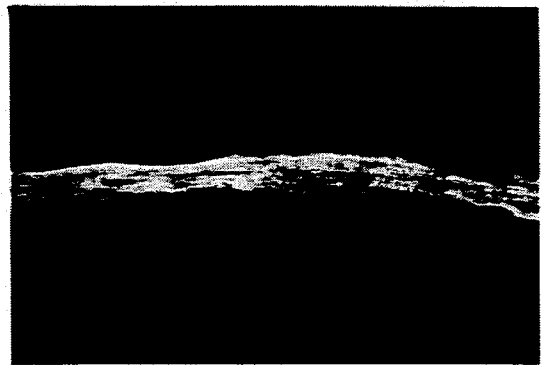
Figure 7:
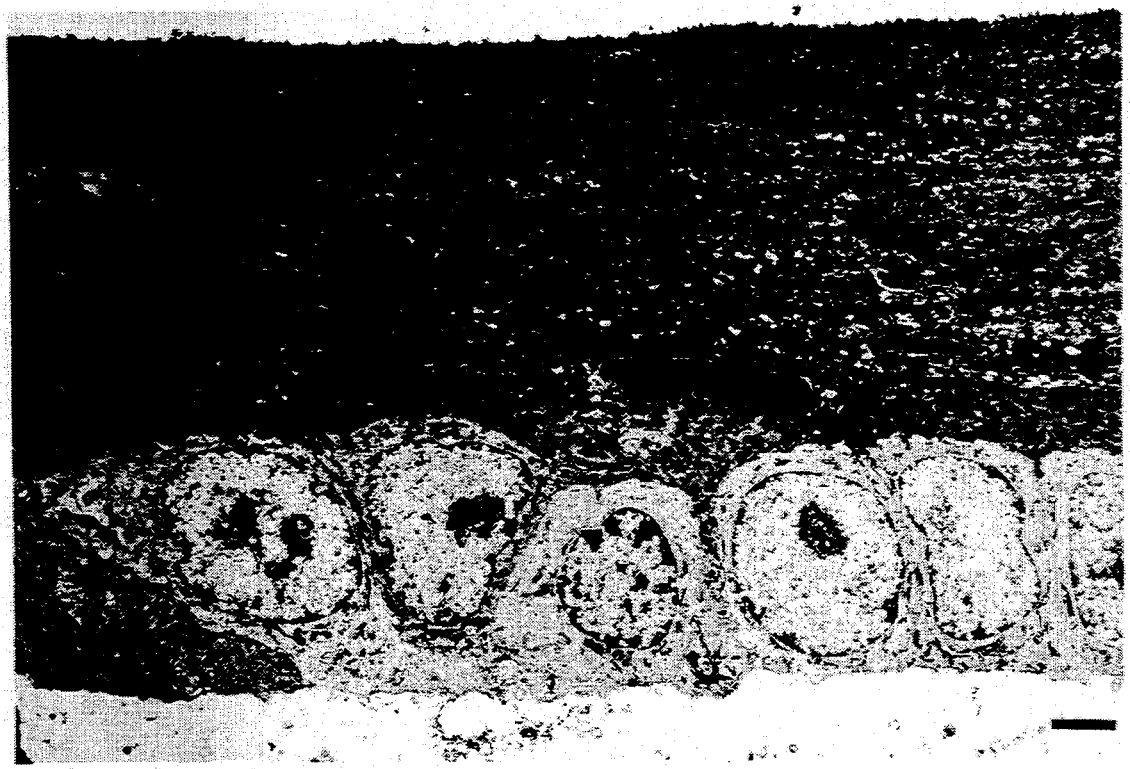
FIGS. 7–10 are transmission electron micrographs of corneal constructs. For transmission electron microscopy, corneal equivalents containing an endothelial, stromal and epithelial cell layer, were fixed at 1 week post-MA/L for 4 hours in a solution of 2.0% paraformaldehyde, 2.5% glutaraldehyde, 1% acrolein and 1% lanthanum nitrate in 0.1M sodium cacodylate, pH 7.4. Samples were post-fixed in 1% OsO4 (in 0.1M sodium cacodylate) and stained en bloc with 2% uranyl acetate (aqueous). Samples were dehydrated in ethanol and embedded in epoxy resin.
Figure 8:
Figure 9:
Figure 10:
Figure 11:
FIG. 11 is a photomicrograph of a corneal equivalent cultured in the presence of an endothelial cell monolayer not in direct contact with the equivalent. A seven day corneal construct with endothelial cells plated as a feeder layer on the bottom of the well rather than incorporated in the lattice. The fibroblasts migrate and multiply under the epithelium pushing (arrows) the epithelium off the lattice. Mag=320X
Figure 12:
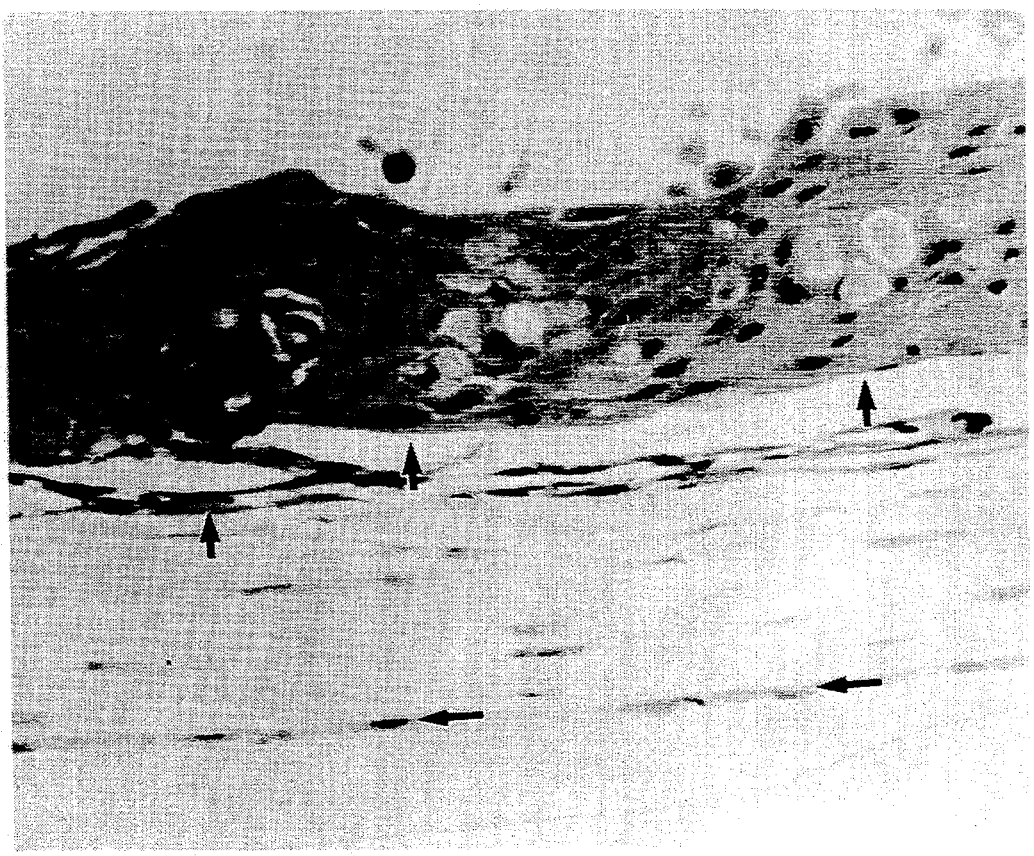
FIG. 12 is a photomicrograph of a corneal equivalent formed with an endothelial cell layer attenuated by treatment with Mitomycin C. A 14 day corneal construct containing endothelial cells was attenuated with mitomycin C. The endothelial cells (arrow) stopped dividing but they were unable to prevent chemotaxis and hyperproliferation of the fibroblasts. The fibroblasts (arrowhead) are pushing the disorganized epithelium off the lattice. Mag=320X
Figure 13A:
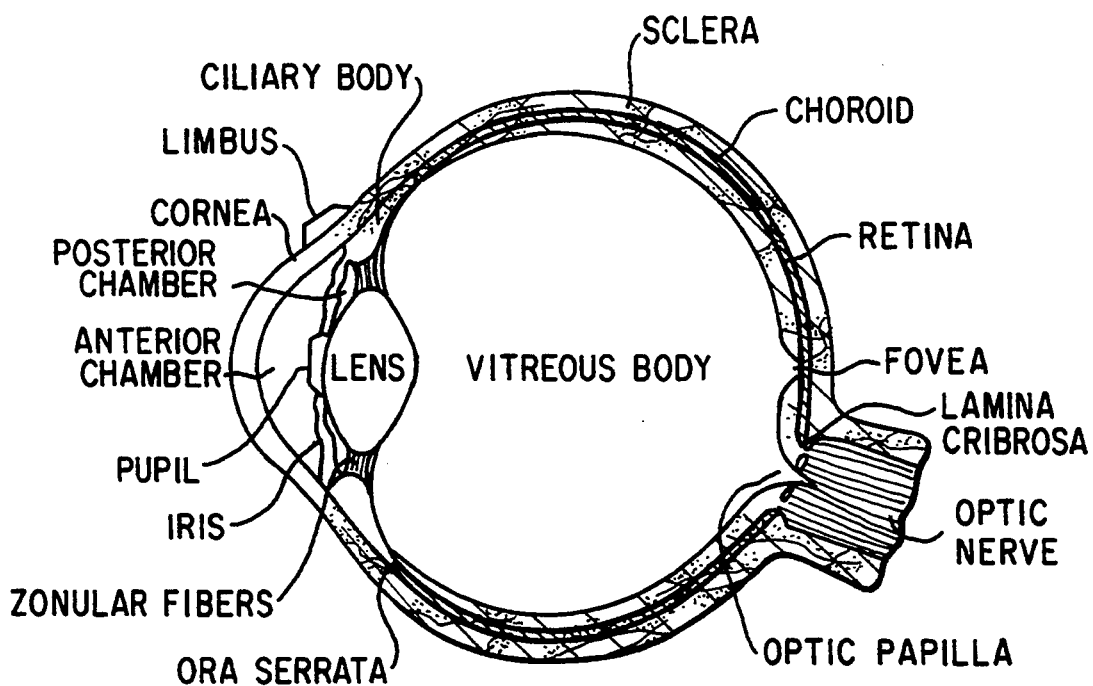
FIG. 13 is a diagram of an eye (13A) cut in a meridional plane that passes through the equator of the eye horizontally, dividing the eye into an upper and a lower half. Diagram (13B) is a section through the human cornea, showing the five layers. (Diagrams from *Functional Histology*, Borysenko et al., Little Brown, publishers, pages 216–217, 1979.)

The outermost layer of the eye is the fibrous tunic, composed of dense avascular connective tissue. The fibrous tunic has two different regions: the sclera and the cornea. The sclera, the "white" of the eye, forms the posterior portion of the fibrous tunic. The anterior sixth of the fibrous tunic is modified to form the transparent cornea. (FIG. 13A.)

Figure 13B:
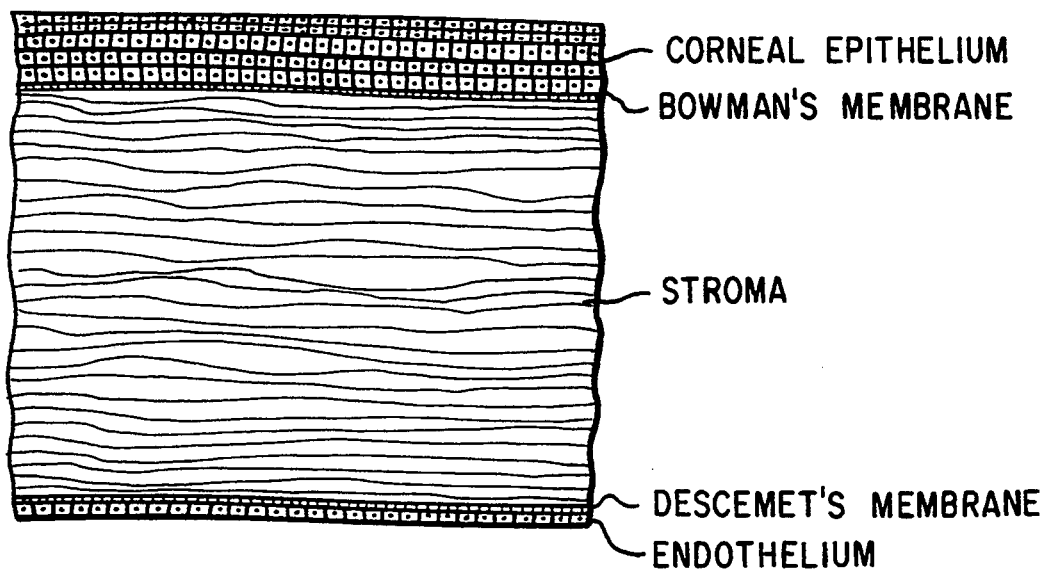

The cornea is covered by an epithelial sheet on both faces. The external sheet, a stratified squamous epithelium, merges with the ocular conjunctiva at the sclera-cornea junction. A simple squamous epithelium, also called the corneal endothelium, lines the inner face of the cornea. The middle layer of the cornea is clear, the result of the regular arrangement of its collagen fibers. There are two membranes separating the stroma from the epithelial layer and the endothelial layer: Bowman's membrane and Descemet's membrane. (FIG. 13B.)

1. Construction of an In Vitro Cornea Model

Constructing the cornea equivalent according to this invention involves the tissue culturing and generation of the three distinct cell layers in the cornea: the external layer, a stratified squamous epithelium; the middle layer, collagen fibers; and the inner layer, a simple squamous epithelium, also called the corneal endothelium. The method of constructing the cornea equivalent results in a structure analogous to the eye cornea in vivo.

The following description of the preferred embodiment of the cornea equivalent is meant to be illustrative and not limiting. Modifications can be made to the cells and to the culturing parameters and still be within the scope of the invention.

In the first step of constructing the in vitro cornea model, the endothelial cells are seeded onto membranes of a cell culture insert.

The walls of the cell culture insert may consist of polystyrene, polycarbonate, resin, polypropylene (or other biocompatible plastic) with a porous membrane base of polycarbonate or other culture compatible porous membrane such as membranes made of collagen, cellulose, glass fiber or nylon attached to the bottom on which cells can be cultured. The porosity of the membrane can vary from 0.2 um to 10 um, with 3 um being preferable. The insert is either suspended or supported in the culture dish to allow culture medium to access the underside of the culture. An acellular collagen layer is cast onto the cell culture membrane and allowed to gel at room temperature. The amount of acellular layer cast will depend upon the cell culture membrane used, but will typically be from 1 mL to about 5 mL.

In the preferred method, a K-RESIN ® culture insert with a 3 um porous polycarbonate membrane base approximately 2 $cm^2$ in area is used. A 1 mL acellular layer is cast onto the polycarbonate membrane and allowed to gel. The acellular collagen layer comprises 686 ug acid extracted bovine tendon collagen in 0.05% acetic acid, 8.1% 10X Minimal Essential Eagle Medium, 4 mM 1-glutamine, 50 ug/ml gentamicin, 1.8 mg/ml sodium bicarbonate and 10% Dulbecco's modified Eagle's medium (DMEM) containing 10% newborn calf serum (NBCS). Once this has gelled, $3 \times 10^4$ endothelial cells ($6.7 \times 10^3/cm^2$) are seeded onto the gel. The endothelial layer is then submerged in DMEM containing 10% NBCS, 4 mM 1-glutamine, and 50 ug/ml gentamicin for four days at 37° C., 10% $CO_2$. Alternatively, the acellular collagen layer may be omitted and the endothelial cells seeded directly onto the porous membrane. The use of an acellular layer is preferable when using transformed endothelial cells to inhibit overgrowth of the non-contact-inhibited cells on the underside of the membrane. Alternatively, the acellular layer may be made of Type IV collagen, laminin or a hydrogel.

The endothelial cells used to form the endothelial layer can be derived from a variety of sources. Corneal endothelial cells derived from sheep, rabbit and mouse have been used. The mouse endothelial cells were transformed with large T antigen of SV40 (Muragaki, et al., 1992). The preferred cell types are the transformed mouse corneal endothelial cell line, or normal corneal endothelial cells derived from sheep or rabbit. Most preferable are normal rabbit corneal endothelial cells. The normal endothelial cells are derived from enzymatically dissociated corneal endothelium or from explants of cornea and are serially cultivated in MSBM medium (Johnson et al., 1992) modified by the addition of 50 ug/mL heparin and 0.4 ug/mL heparin binding growth factor-1 (MSBME). Transformed endothelial cells are cultivated in DMEM-10% NBCS.

Endothelial cells from a noncorneal origin may also be used in this invention. The noncorneal origin endothelial cells that may be used in this invention include vascular and human umbilical vein endothelial cells.

The endothelial cells may be transformed with a recombinant retrovirus containing the large T antigen of SV40 (Muragaki, et al., 1992). Transformed cells continue to grow in the corneal equivalent and form mounds on top of the acellular layer due to their lack of contact inhibition. Non-transformed cells will form a monolayer underlying the stromal cell-collagen layer. Alternatively, normal endothelial cells may be transfected as above, but with the addition of a heat sensitive gene. This will allow the cells to grow in continuous culture under reduced temperature. After establishment of a confluent endothelial cell layer, the temperature can be raised to deactivate the transforming gene, allowing the cells to resume their normal regulation and exhibit contact inhibition, to form an endothelial cell monolayer similar to the non-transformed cells. Most peptides are heat sensitive (with the exception of heat shock proteins) so that there is a wide choice of peptides that can be deactivated by raising culturing temperature. Transformation in this way also facilitates the use of hard to obtain and cultivate cell types such as human corneal endothelial cells.

In the second step, collagen is mixed with corneal keratocytes (stromal fibroblast cells) to achieve a cell-collagen mixture. The cell-collagen mixture contains approximately 100 stromal fibroblast cells per ug acid extracted bovine tendon collagen. The fibroblasts contract the gel to form a raised area (mesa) of approximately 2.5 $cm^2$.

The type of collagen that can be used are acid extracted bovine tendon collagen, enzyme extracted bovine tendon collagen, or rat tail collagen. Alternatively, the collagen may also consist of a mixture of Types I and III collagen as commonly extracted from dermis or a mixture of Types I, V and VI as extracted from corneal stroma. Preferably, purified acid-extracted Type I collagen extracted from bovine tendon is used for the initial gel. In the organotypic construct, the stromal fibroblasts will synthesize additional collagen types such as V and VI as well as additional Type I collagen as they modify the collagen matrix during cultivation. The epithelial cells will contribute Type IV and VII collagen at the epithelial-stromal junction and the endothelial cells will contribute Type XII collagen (Muragaki, et al., 1992) at the endothelial-stromal junction.

Any mammalian stromal fibroblast may be used in this cell layer. Any connective tissue fibroblast such as those derived from sclera, dermis, tendon, or fascia may be used. When corneal cells are used, fibroblasts derived from rabbit or human corneal stroma are preferable. The cells are enzymatically dissociated from normal corneal stroma, cultured in DMEM-10% NBCS and serially passaged. The cells incorporated into the construct are used at passage four.

Once the endothelial cell culture is ready, to prepare for the second layer of cells, the cell-collagen mixture, the medium is removed from the cell culture inserts containing the confluent endothelial layer (typically $1.7-2.5 \times X10 \times 5$ cells/insert). The cell-collagen mixture is transferred and contacted with the surface of the endothelial cell layer. The cell-collagen mixture contains the same proportions of materials as the acellular layer with the addition of $5 \times 10^4$ stromal fibroblasts/mL cast mixture. Three mL of this mixture is pipetted into each cell culture insert and allowed to gel. The construct is then submerged in DMEM-10% NBCS and allowed to contract at 37° C., 10% $CO_2$ for seven days.

These two layers, which will eventually comprise the endothelial layer and the collagen layer of the cornea model, are cultured under culturing conditions, known to those of skill in the art, to form a condensed collagen lattice, preferably by submerging in Dulbecco's-10% NBCS at 37° C., 10% $CO_2$ for seven days, to form a central raised area or a "mesa," resulting from the contraction of the collagen by the stromal fibroblasts forming a condensed collagen lattice. Normal rabbit stromal fibroblasts are cultured for seven days, but culture may be shorter or longer (normally 2-10 days) depending on the species, cell type and number used. DMEM 10% NBCS is the preferred culture medium but any medium which normally supports the growth of fibroblasts may be used.

In the third step, once the condensed collagen lattice is formed, corneal epithelial cells are plated onto the raised area of the collagen. The corneal epithelial cells can be derived from a variety of mammalian sources. The preferred epithelial cell is a rabbit or human corneal epithelial cell (corneal keratinocyte) but any mammalian corneal keratinocyte may be used. Other epithelial keratinocytes such as those derived from the sclera (outer white opaque portion) of the eye or epidermis may be substituted, but corneal keratinocytes are preferable.

The medium is removed from the culture insert (containing the contracted stromal matrix and endothelial layer) and its surround. Normal rabbit corneal epithelial cells, passage 4, are trypsinized and seeded on top of the membrane at a density of $7.2 \times 10^4$–$1.4 \times 10^5$ cells/$cm^2$. The constructs are then incubated without media for four hours at 37° C., 10% $CO_2$ to allow the epithelial cells to attach. After the incubation the constructs are submerged in Corneal Maintenance Medium (CMM) (Johnson et al., 1992.)

The epithelial cells are cultured until the mesa is covered with the epithelial cells. Completeness of epithelial coverage can be ascertained by a variety of methods, for illustration by staining the culture with a solution of Nile Blue sulfate (1:10,000 in phosphate buffered saline).

Once the mesa is covered, after approximately seven days, the constructs are aseptically transferred to new coculturing trays with sufficient cornea maintenance medium (CMM) to achieve a fluid level just to the surface of the construct to maintain a moist interface without submersion of the epithelial layer. The constructs are incubated at 37° C., 10% $CO_2$, and greater than 60% humidity, with the CMM, making media changes, as necessary, typically, three times per week.

As used herein, the term "moist interface" is intended to mean a culture environment which is regulated so that the surface of the construct is moist, with high humidity, but not dry or submerged. The exact level of moisture and humidity in the culture environment is not critical, but it should be sufficiently moist and humid to avoid the formation of cornified cells. A moist interface can be characterized as trying to duplicate similar moisture levels of the human eye.

Morphological and immunocytochemical comparison of incubation of the construct at (1) a true air interface (dry) versus (2) incubation submerged versus (3) incubation moist, but not submerged, showed that only the moist or dry interfaces yielded an epithelium which approached normal cornea. Incubation at a dry interface, however, caused the corneal epithelium to undergo abnormal squamous (skin-line) differentiation.

There are several alternatives to achieve a moist interface of the epithelial layer and the media.

An alternative method of achieving a moist interface at the epithelial layer utilizes a lipid/mucin mixture to simulate tear film. The specialized tear film may be formulated using a physiologic buffered salt solution containing protein-lipid surfactants or lipids and/or mucin, glycosaminoglycans, hyaluronic acid or other moisture holding substance. The film droplet is placed on top of the mesa to maintain a moist barrier between the epithelium and the atmosphere. The film is typically replaced when the media is changed. Alternatively, one or more of the components of the tear film can be added directly to the medium and allowed to wick over the surface of the construct during culture to form the moist surface interface.

Alternatively, maintenance of a moist interface may also be aided by the use of an artificial layer which can draw and hold moisture over the surface of the culture. This can be achieved by the application of a thin layer made of agarose, hydrogel, or alginate.

In another alternative, a moist interface can be achieved using a dialysis membrane or polymer, such as contact lens material, cut slightly larger than the mesa which, may be used to draw and hold fluid and prevent moisture loss.

2. Use of the Endothelium in Other Organ Equivalents

The inclusion of an endothelial layer promotes improved morphology, expression of biochemical and physiological markers, cell spreading, epithelial attachment to the matrix, and uniformity of epithelial coverage in vivo. The results on the influence of the endothelium in achieving a higher level of epithelial differentiation in vitro and promoting basement membrane formation was applied in other tissue equivalent in vitro culturing methods.

In preparing tissue or organ equivalents using collagen a first layer of endothelial cells can be cultured, as described above in section (1), prior to casting collagen onto the endothelial layer. Examples of tissue equivalents that can be modified according to this invention include, U.S. Ser. No. 07/408,052, incorporated herein by reference. In a preferred embodiment, the endothelial cell layer is used to modify in vitro akin equivalent models, such as those described in U.S. Pat. No. 4,485,096, incorporated herein by reference, to promote epithelial differentiation and basement membrane formation.

3. Uses For The Cornea Equivalent Model

The Draize eye irritation test (Draize et al., 1944) has served as the standard for evaluating a product's ocular irritation potential for the past 45 years.

A variety of test models and protocols have been proposed as in vitro screens for assessing ocular irritation (Booman et al., 1988). Cell cultures used in conjunction with quantifiable, objective endpoints for assessing cytotoxicity have shown good correlations to in vivo data sets (Bruner et al., 1991). However, cells in monolayer culture have inherent limitations as model systems for predicting irritation in complex organs such as the eye. Typically, cells in monolayer culture are susceptible to irritants at concentrations far below those required to induce irritation in vivo. Test samples must first be solubilized in cell culture medium prior to being introduced to the culture system. This can lead to secondary toxicities due to effects on osmolarity, pH or medium components. Furthermore, artifacts arising from diluting the test sample can mask toxicity and lead to underestimating a sample's irritancy potential. The level of epidermal differentiation obtained in monolayer culture only poorly mimics the extent of differentiation observed in vivo. The protective barrier function of corneal epithelium, including cytoskeletal keratin networks, desmosomes and tight junctions, known to play an important role in protecting ocular tissue from chemical insult (Holly, 1985) are not present. The organotypic model proposed here, overcomes some of the inherent limitations of monolayer culture by providing a model system which more closely simulates the target organ of interest. In addition, the physical configuration of this test cornea allows the topical application of test samples in vehicles (e.g., petrolatum and mineral oil) which approximate the mode of exposure in vivo.

Investigators have used both animal models and cultured cells in an effort to approximate the human condition. There is, however, a wide gap in direct applicability. Animals may be too different in their physiological response to injury and analysis using traditional cell culture may be too simplified for direct correlations to likely in vivo human responses. While these methods are necessary and useful, the use of human organotypic constructs helps eliminate the discrepancy between human and animal response, and bridges the gap between cultured cells and the complex organism. Cell-cell interactions and the response to injury or pharmacologic agents may be readily examined in a controlled, organotypic environment.

The organotypic culture method may also be used to form graftable human tissue either as an adjunct to conventional transplantation or as a substitute. The use of cultured corneal endothelial cells has already been shown to be beneficial as a replacement for the often damaged or inadequate endothelium of graft material (Insler and Lopez, 1986). The use of cultured corneal epithelium has also shown some benefit in promoting wound closure (Roar and Thoft, 1988). The organotypic corneal construct comprising an endothelium, stroma and epithelium could be used for ocular wound closure and full-thickness repair of the cornea. Although not transparent in vitro, it is expected that the endothelial cells provided by the construct will regulate fluid transport to the corneal stroma and further stimulate the stromal fibroblasts to continue to organize the matrix and produce the appropriate collagens and glycosaminoglycans necessary for corneal clarity. The in vitro corneal equivalent may be constructed with more or less extracellular matrix or stroma to facilitate remodeling. Wound closure would be maintained by the presence of the well-adhered corneal epithelium, thereby limiting hyperproliferation and scaring of the stromal matrix.

The invention is illustrated further by the following examples, which are not to be taken as limiting in any way.

EXAMPLES

Example 1

The corneal maintenance medium (CMM) used in the construction of the cornea equivalent had the following components:

3:1 Calcium-free Dulbecco's modified Eagle's Medium:Ham's F-12
1.1 uM hydrocortisone
5 ug/ml Insulin
5 ug/ml Transferrin
20 pM Triiodothyronine
$10^{-4}$M Ethanolamine
$10^{-4}$M O-phosphoryl-ethanolamine
1 mM Strontium chloride
50 ug/ml Gentamicin
4 mM 1-glutamine
90 uM Adenine
$3 \times 10^{-6}$M Selenium
1.8 mM Calcium Chloride
0.3% NBCS

Example 2

The model employing an endothelial cell layer and a moist interface, two key features of which have been made the following way:

Serially passaged mouse corneal endothelial cell line or normal rabbit corneal endothelial cells were trypsinized and seeded onto membranes of a cell culture insert (such as a Costar transwell) at $3 \times 10^4$ cell/insert in DMEM 10% newborn calf serum or serum-free medium (MSBME) and incubated at 37° C., 10% $CO_2$ for 4 days.

A mixture of bovine Type I acid extracted collagen (0.9-1.2 mg/ml in 0.5% acetic acid) was neutralized at 4° C. using 10X concentrated MEM, containing sodium bicarbonate, 10% newborn calf serum, and 20 mM l-glutamine. The cold neutralized collagen mixture was mixed with a suspension of serially passaged rabbit corneal keratocytes (stromal cells) to yield a final cell concentration of $5 \times 10^4$ keratocytes/ml.

The medium was removed from the endothelial cell cultures and 3 ml of the cell-collagen mixture was pipetted onto the surface of the endothelial cell layer. The collagen gel was then warmed to form a cellular collagen gel. The gel was contracted by the keratocytes to form a condensed collagen lattice with a central raised area or "mesa" in approximately 7 days, which was underlaid with the endothelial layer.

On day 7, serially passaged corneal epithelial cells were trypsinized and plated onto the mesa at a concentration of $1.8 \times 10^5$ cells/mesa. Constructs were incubated in a humidified incubator at 37° C., 10% $CO_2$ for 4 hours to allow attachment of cells to the collagen matrix. Constructs were then incubated, submerged, in 13 ml of corneal maintenance medium (CMM). The media was changed 3 times per week.

On day 7 post-epithelialization, one sample was stained with a solution of Nile Blue sulfate (1:10,000 in phosphate buffered saline) to check for completeness of epithelial coverage.

If the mesa was 100% covered, the constructs were aseptically transferred to new trays which contained 11 mls of medium and 2 cotton pads to support the culture insert and prevent meniscus formation. 11 ml of medium achieved a fluid level just to the surface of the construct (which was 1 mm or less in thickness at this time). This maintained a moist surface without submersion. The constructs were then incubated as above with media changes 3 times/week, each time exchanging 9 ml of medium (the cotton pads held the remaining 2 ml).

Example 3

The Effect of Environment of Corneal Differentiation

After the epithelialized corneal constructs were cultured for one week in CMM, they were either left submerged, lifted on cotton pads to a dry air-liquid interface or lifted on cotton pads with enough media to provide a moist, yet not submerged epithelial surface. The dry interface was achieved by removing the cell culture insert from its carrier and placing it on top of two cotton pads suspended in a culture well, deep well tray or dish containing enough medium to just reach the cotton pads. Medium was wicked through the cotton pads to the undersurface of the culture. The moist interface was achieved in a similar way, but the volume of media surrounding the pads was increased to bring the fluid level to the shoulders of the mesa (central raised area of the construct). Typically, in a deep well culture tray with two cotton pads, nine mL of medium achieved a dry interface and eleven mL of medium achieved a moist interface. Medium was naturally drawn over the surface of the mesa, without submerging the epithelial surface on the top of the mesa.

Morphological and immunocytochemical comparison of incubation of the construct at a true air interface (dry) versus incubation submerged versus incubation moist showed that only the moist or dry interface yielded an epithelium which approached normal limbal cornea in distribution of vinculin and alphaenolase. Culture at a dry interface, however, caused the corneal epithelium to undergo abnormal squamous (skin-like) differentiation.

Example 4

Inclusion of the Endothelial Cell Layer

Inclusion of an endothelial cell layer makes the construct more reproducible and manufacturable. It improved outgrowth of the corneal epithelium on the matrix, improved physical attachment of the epithelial layer (easily separable from the matrix without endothelium, inseparable with) and eliminated keratocyte overgrowth in and onto the collagen surface (without the endothelium, the stromal keratocytes appeared hyperproliferative, and were drawn out of the lattice by what appears to be chemotactic properties of the epithelium, then competing with the epithelial cells for the lattice surface).

Example 5

Effects of Inclusion of an Endothelial Cell Layer

Inclusion of the endothelial layer also yielded a construct with greater organotypic character. Immunochemical studies comparing moist constructs with and without an endothelial layer showed the enhanced expression of Type VII collagen, the component of anchoring filaments and laminin, a component of basement membrane. (Basal lamina and cell-matrix interaction are important components in studying corneal wound repair; lack of these components would lessen the utility of a corneal construct.) Three-layered constructs also showed even greater limbal-like localization of alpha-enolase (being restricted to the basal layer of the corneal epithelium).

Example 6

Ultrastructural Specializations of the Corneal Equivalent

Morphological differentiation of the three-layer construct showed the presence of organized basal lamina, lack of abnormal squamous differentiation and the presence of characteristic vermiform ridges on the epithelial surface.

Example 7

Direct contact of the endothelial cell layer with the stromal lattice is necessary for optimal effect.

Transformed mouse corneal endothelial cells were plated in six-well tissue culture dishes ($6.7 \times 10^3$ cells/cm$^2$) in DMEM $-10\%$ NBCS and allowed to grow to confluence. A cell culture insert containing an uncontracted stromal lattice was placed into the well, allowing the conditioned medium from the endothelial layer to bathe the lattice while it contracted for seven days. On day seven, the stromal construct was epithelialized as normal and cultured in the presence of the endothelial cell layer for seven days. Samples were analysed by histology. The results were similar to Example 3 with a disorganized epithelium and fibroblast chemotaxis. Plating the endothelial cells on the bottom of a culture dish separated from direct contact with the stromal layer also did not achieve the desired results.

Example 8

Attenuation of endothelial cells with Mitomycin C inhibits their effect in the corneal equivalent.

Transformed mouse endothelial cells do not exhibit contact inhibition of growth, as a result, they continued to multiply forming multilayers and mounds of cells beneath the stromal lattice. Studies were done in an attempt to attenuate the cells with Mitomycin C prior to formation of the stromal lattice.

Transformed mouse endothelial cells were seeded directly onto the polycarbonate membranes of the cell culture inserts and allowed to grow to confluence. Prior to casting the stromal layer, the endothelial cells were incubated at 37° C., 10% $CO_2$ for one or two hours in medium containing either 2 or 4 ug/ml Mitomycin C. The endothelial cells were washed twice with DMEM $-10\%$ NBCS and the stromal layer pipetted on top. The Mitomycin C treatment prevented endothelial cell overgrowth and promoted epithelial development, however, it was not able to prevent fibroblast chemotaxis. Attenuation of the mouse endothelial cells with Mitomycin C to prevent further division of the mouse endothelial cells (which lack contact inhibition presumably due to their SV40 transformation) reduced the effect of the endothelial layer.

Example 9

Development of functional barrier properties in the corneal equivalent.

The presence of functional tight junctions was verified using a fluorescein permeability assay. The permeability barrier improved over time as shown below. It was also apparent that providing cultures with a moist interface improved the permeability barrier. In addition, the permeability barrier can be improved by using different strains of cells. The difference between two strains of rabbit corneal epithelium is shown below.

Corneal constructs in the cell culture inserts were placed in six well dishes containing two mls of Hanks Balanced Salt Solution (HBSS) with Calcium and Magnesium. A polycarbonate ring was placed on top of the mesa and sealed with a bead of silicone grease to prevent seepage. This exposed a surface area of 0.785 cm$^2$. A 50 ul drop of sodium fluorescein (0.5 mg/ml in HBSS) was pipetted into the ring on top of the corneal epithelium and allowed to incubate, covered in foil, for thirty minutes at room temperature. The absorbance of fluorescein in the HBSS in the well was measured on the spectrophotometer at 490 nm. Typical results are shown below. The moist cultures showed greater resistance to fluorescein permeability suggesting the development of tight junctions. Permeability was seen to vary depending on the quality (as judged by appearance, growth characteristics) of the epithelial cell strain.

| | |
|---|---|
| PLAIN FILTERS (CONTROL) | 2.565 |
| | 2.552 |
| | 2.549 |
| RABBIT EPITHELIAL STRAIN 1259 | |
| 9d Moist Interface: | 0.322 |
| | 0.343 |
| | 0.347 |
| 9d Submerged: | 1.830 |
| 14d Moist Interface: | 0.130 |
| | 0.102 |
| | 0.821 |
| 14d Submerged: | 0.932 |
| | 0.508 |
| | 0.616 |
| RABBIT EPITHELIAL STRAIN 12129 | |
| 9d Moist Interface: | 0.064 |
| | 0.054 |
| | 0.037 |
| 14d Submerged: | 0.030 |
| | 0.023 |
| | 0.03 |

Although the foregoing invention has been described in some detail by way of illustration and example for purposes of clarity of understanding, it will be obvious to one skilled in the art that certain changes and modifications may be practiced within the scope of the appended claims.

What is claimed is:

1. A cornea equivalent comprising:
   (a) an inner endothelial cell layer, wherein said endothelial cells are derived from mammalian corneal endothelial cells;
   (b) a middle stromal cell-collagen mixture layer, wherein said stromal cells are derived from mammalian corneal stromal fibroblast cells; and
   (c) an external epithelial cell layer, wherein said epithelial cells are derived from mammalian corneal epithelial cells.

2. The cornea equivalent of claim 1, wherein said endothelial cells of said inner endothelial cell layer are derived from mammalian corneal endothelial cells transformed with the large T antigen of SV40.

3. The cornea equivalent as in either claim 1 or claim 2 wherein the collagen in said middle stromal cell-collagen mixture layer is selected from the group consisting of acid extracted bovine tendon collagen, enzyme extracted bovine tendon collagen, rat tail collagen, Type I collagen extracted from dermis, Type III collagen extracted from dermis, Type I collagen extracted from corneal stroma, Type V extracted from corneal stroma, and Type VI collagen extracted from corneal stroma.

4. The cornea equivalent of claim 3, wherein said collagen is a mixture of Types I and III collagen extracted from dermis.

5. The cornea equivalent of claim 3, wherein said collagen is a mixture of Types I, V and VI collagen extracted from corneal stroma.

6. The method of producing a cornea equivalent comprising:
   (a) culturing endothelial cells to form an inner endothelial cell layer, wherein said endothelial cells are derived from mammalian corneal cells;
   (b) mixing stromal cells with collagen to achieve a stromal cell-collagen mixture, wherein said stromal cells are derived from mammalian corneal stromal fibroblast cells;
   (c) contacting said inner endothelial cell layer of step (a) with said stromal cell-collagen mixture of step (b), thereby forming a middle layer provided on said inner layer;
   (d) culturing said inner endothelial cell layer and said middle layer;
   (e) contacting epithelial cells onto said middle layer of step (d), wherein said epithelial cells are derived from mammalian corneal epithelial cells;
   (f) culturing said epithelial cells with said middle layer until said middle layer is covered with an external layer of epithelial cells; and,
   (g) continue culturing said inner, middle, and external layers under conditions to achieve a moist interface and forming a cornea equivalent.

7. The method of claim 6, wherein said endothelial cells of step (a) are derived from mammalian corneal endothelial cells transformed with the large T antigen of SV40.

8. The method as in either claim 6 or claim 7, wherein said endothelial cells are cultured in said first step by contacting said endothelial cells onto a porous membrane attached to the bottom of a cell culture insert.

9. The method of claim 8 wherein said porous membrane has a porosity of from about 0.2 micrometers to 10 micrometers.

10. The method of claim 8 wherein prior to said contacting, an acellular collagen layer is cast onto said porous membrane.

11. The method as in either claim 6 or claim 7, wherein the collagen in said stromal cell collagen mixture is selected from the group consisting of acid extracted bovine tendon collagen, enzyme extracted bovine tendon collagen, rat tail collagen, Type I collagen extracted from dermis, Type III collagen extracted from dermis, Type I collagen extracted from corneal stroma, Type V collagen extracted from corneal stroma, and Type VI collagen extracted from corneal stroma.

12. The method as in either claim 6 or claim 7, wherein said stromal cell-collagen mixture of said step (b) contains approximately 100 corneal stromal fibroblast cells per microgram collagen or $5 \times 10^4$ corneal stromal fibroblast cells/mL collagen and said collagen.

13. The method as in either claim 6 or claim 7, wherein said inner endothelial cell layer and said middle layer of said step (d) are cultured until said middle layer contracts to form a central raised area.

14. The method as in either claim 6 or 7, wherein said epithelial cells in said third step (e) are seeded on top of said middle layer of step (b) at a density of $7.2 \times 10^4 - 1.4 \times 10^5$ cells/cm$^2$.

15. The method as in either claim 6 or claim 7, wherein said moist interface of said third step (g) is achieved by placing a droplet of tear film onto said external layer of epithelial cells or adding said tear film directly to the culture medium.

16. The method of claim 15, wherein said tear film comprises physiologic buffered salt solution.

17. The method of claim 16, wherein said physiologic buffered salt solution includes one or more components selected from the group consisting of protein-lipid surfactants, lipids, mucin, glycosaminoglycans, and hyaluronic acid.

18. The method as in either claim 6 or claim 7, wherein said moist surface interface of said third step (c)

(iii) comprises a moisture loss prevention layer or membrane.

19. A cornea equivalent comprising:
   (a) an inner endothelial cell layer, wherein said endothelial cells are derived from the mammalian endothelial cells;
   (b) a middle stromal cell-collagen mixture layer, wherein said stromal cells are mammalian stromal fibroblasts derived from the group comprising sclera, dermis, tendon or fascia; and
   (c) an external epithelial cell layer, wherein said epithelial cells are mammalian epithelial keratinocytes derived from the group comprising corneal keratinocytes and scleral keratinocytes.

20. The method of producing a cornea equivalent comprising:
   (a) culturing mammalian endothelial cells to form an inner endothelial cell layer;
   (b) mixing mammalian stromal cells with collagen to achieve a stromal cell-collagen mixture, wherein said stromal cells are mammalian stromal fibroblasts derived from sclera, dermis, tendon or fascia;
   (c) contacting said inner endothelial cell layer of step (a) with said stromal cell-collagen mixture of step (b), thereby forming a middle layer provided on said inner layer;
   (d) culturing said inner endothelial cell layer and said middle layer;
   (e) contacting mammalian epithelial cells onto said middle layer of step (d), wherein said epithelial cells are mammalian epithelial keratinocytes selected from the group consisting of corneal keratinocytes and scleral keratinocytes;
   (f) culturing said epithelial cells with said middle layer until said middle layer is covered with an external layer of epithelial cells; and,
   (g) continue culturing said inner, middle, and external layers under conditions to achieve a moist interface and forming a cornea equivalent.

21. The cornea equivalent as in either claim 1 or claim 2 wherein said middle stromal cell-collagen mixture layer is uniform in thickness.

22. The cornea equivalent as in either claim 1 or claim 2 wherein said external epithelial cell layer is uniform in thickness.

23. The cornea equivalent as in either claim 1 or claim 2 wherein the suprabasal cells of said external epithelial cell layer exhibit reduced alpha-enolase activity.

24. The cornea equivalent as in either claim 1 or claim 2 wherein the suprabasal cells of said external epithelial cell layer expresses keratin 3.

25. The cornea equivalent as in either claim 1 or claim 2 wherein the junction between said middle stromal cell-collagen mixture layer and said external epithelial cell layer expresses laminin and type VII collagen.

26. The cornea equivalent as in either claim 1 or claim 2 wherein the junction between said middle stromal cell-collagen mixture layer and said external epithelial cell layer has a basement membrane.

27. The cornea equivalent as in either claim 1 or claim 2 wherein said external epithelial cell layer exhibits vermiform ridges on the epithelial surface.

28. The cornea equivalent as in either claim 1 or claim 2 wherein the suprabasal cells of said external epithelial cell layer exhibit tight junctions between cells.

* * * * *